(12) United States Patent
Osborne

(10) Patent No.: US 7,399,462 B2
(45) Date of Patent: Jul. 15, 2008

(54) PROTECTANT FOR UV-INDUCED SKIN DAMAGE

(75) Inventor: David W. Osborne, Fort Collins, CO (US)

(73) Assignee: QLT USA, Inc., Fort Collins, CO (US)

( * ) Notice: Subject to any disclaimer, the term of this patent is extended or adjusted under 35 U.S.C. 154(b) by 325 days.

(21) Appl. No.: 11/011,291

(22) Filed: Dec. 14, 2004

(65) Prior Publication Data

US 2005/0186156 A1    Aug. 25, 2005

Related U.S. Application Data

(63) Continuation of application No. 10/284,682, filed on Oct. 30, 2002, now abandoned.

(51) Int. Cl.
*A61Q 17/00* (2006.01)
*A61Q 17/04* (2006.01)
*A61Q 19/00* (2006.01)

(52) U.S. Cl. .................... 424/59; 424/401; 424/449

(58) Field of Classification Search ............... 424/59
See application file for complete search history.

(56) References Cited

U.S. PATENT DOCUMENTS

| | | | |
|---|---|---|---|
| 5,863,560 A | 1/1999 | Osborne | |
| 6,060,085 A | 5/2000 | Osborne | |
| 6,071,543 A | 6/2000 | Thornfeldt | |
| 6,113,888 A | 9/2000 | Castro et al. | |
| 6,200,964 B1 | 3/2001 | Singleton et al. | |
| 6,231,837 B1 | 5/2001 | Stroud et al. | |
| 6,482,839 B1 | 11/2002 | Thornfeldt | |
| 2004/0092583 A1 | 5/2004 | Snanahan-Prendergast | |

FOREIGN PATENT DOCUMENTS

| | | |
|---|---|---|
| DE | 19654445 | 7/1998 |
| WO | WO-98/53822 A1 | 12/1998 |
| WO | WO-01/41772 A1 | 6/2001 |
| WO | WO-02/053138 A2 | 7/2002 |
| WO | WO 02053138 A2 * | 7/2002 |

OTHER PUBLICATIONS

S. Stockel, Dapsone-induced photodermatitis in a patient with linear IgA dermatosis, Jan.-Feb., Clinical report, vol. 11, pp. 50-53, 2001.*
Igawa, K., et al., "Anti-Oxidative Therapy With Oral Dapsone Improved HCV Antibody Positive Annular Elastolytic Giant Cell Granuloma", *Journal of Dermatology*, 24, (1997), 328-331.
Stöckel, S., et al., "Dapsone-Induced Photodermatitis in a Patient With Linear IgA Dermatosis", *European Journal of Dermatology*, 11, (Jan.-Feb. 2001), 50-53.
Wolf, R., et al., "Dapsone: Unapproved Uses or Indications", *Clinics In Dermatology*, 18, (2000), 37-53.
U.S. Appl. No. 10/081,050, filed Feb. 20, 2002, Osborne.
Forbes, P. D., et al., "Drug Products and Photocarcinogenesis", *In Photobiology, The Science and Its Applications*, Riklis, E. Ed., Plenum Press: New York, New York,(1991),663-669.

* cited by examiner

*Primary Examiner*—Shelley A. Dodson
(74) *Attorney, Agent, or Firm*—Schwegman, Lundberg & Woessner P.A.

(57) ABSTRACT

The present invention provides a method for protecting against UV radiation-induced skin damage. Specifically, compositions including dapsone are administered to provide UV protection. The dapsone compositions may be administered orally, or by other parenteral routes, such as topically, transdermally, by inhalation, and the like.

25 Claims, 1 Drawing Sheet

PROTECTANT FOR UV-INDUCED SKIN DAMAGE

CROSS-REFERENCE TO RELATED APPLICATIONS

This application is a continuation of U.S. patent application Ser. No. 10/284,682, filed on Oct. 30, 2002, now abandoned the specification of which is incorporated herein by reference.

FIELD OF THE INVENTION

The present invention relates to the field of dermatologic pharmacology. In particular, UV protectants that reduce the risk of skin damage are described. The compositions are formulated with dapsone as the active protective ingredient.

BACKGROUND OF THE INVENTION

Human skin is a-primary target of nonionizing electromagnetic radiation in the ultraviolet, visible, and infrared ranges, and consists of three distinct layers: the stratum corneum, the epidermis, and the dermis. The epidermis and dermis contain several molecules known as chromophores, that are capable of absorbing light or UV radiation (UVR). The main chromophores in human skin include such molecules as nucleic acids, aromatic amino acids, proteins, porphyrins, carotenoids, steroids, and quinones (Mary S. Matsui and Vincent A. DeLeo, *Skin Cancer: Mechanisms and Human Relevance* Chp. 4, 22 (Hasan Mukhtar ed., 1995)).

The UV spectrum is divided into A, B, and C ranges. The UVC range extends from wavelengths between 200 and 290 nm. The UVB spectrum includes wavelengths between 290 and 320 nm, and is generally known as the sunburn spectrum because it produces erythema in human skin. UVA radiation includes wavelengths between 320 to 400 nm. Atmospheric ozone absorbs all UVC and much of the UVB, so that the spectrum of UV radiation at the earth's surface consists primarily of UVA. The depth to which a photon penetrates in vivo is related to its wavelength. Thus, most UVB radiation transmitted through the ozone layer is absorbed within the first 0.03 mm of the epidermis, whereas one third of UVA radiation penetrates to a depth of 0.1 mm (Hardie et al., *Surgery* 87:177 (1980)).

When the skin is exposed to UVR, energy transferred to chromophores from the absorbed radiation may result in molecular reorganization and/or interaction with nearby biomolecules. For example, after UVR absorption, DNA may form dipyrimidine lesions, such as cyclobutane pyrimidine dimers. In turn, characteristic mutations result, e.g., mutations in p53, that have been shown to be important in producing non-melanoma skin cancer. (A. Ziegler et al., *Nature* 372:773-776 (1994)). Furthermore, the UV-induced conversion of urocanic acid from the trans to cis isomer has been linked to the subsequent development of non-melanoma skin cancers (Craig A. Elmets et al., *Skin Cancer: Mechanisms and Human Relevance* Chp. 18, 230 (Hasan Mukhtar ed., 1995)).

Further insight into UV-induced skin tumor formation has been gained from studies in rodents. UV-induced skin tumors stimulate a strong immune response. If UV-induced tumors are implanted into normal, genetically identical mice, they are promptly rejected by the host immune-system and the animals survive. If the same tumor is implanted into mice that have been exposed to subcarcinogenic doses of UVR, immunological destruction of the tumor does not occur. These results indicate that UVR produces mutations in skin cells and facilitates tumor growth by impairing immune surveillance. The presence of both deficiencies is necessary for clinically apparent skin cancers to develop (J. T. Krutmann and C. A. Elmets eds. (1995). *Photoimmunology*. Oxford: Blackwell Scientific).

Currently marketed sunscreens function either as ultraviolet (UV) filters or UV blocks. UV blocks, such as $TiO_2$ and ZnO, as well as derivatives of other metal-oxides, form a physical barrier that scatters UV light. These UV blocks offer the most comprehensive sunscreen protection, blocking the full spectrum of UVA and UVB light. However, the most commonly used sunscreens are UV filters, which are typically organic compounds. A disadvantage of UV filters is that each organic compound has a limited range of maximum UV absorptivity, rendering each reagent better suited for either UVA protection or UVB protection, but not both.

The UV-induced mouse tumor model has proven very useful not only in gaining mechanistic understanding of skin tumor formation, but also in determining if topical products promote or inhibit the formation of UV-induced tumors. A standard UV carcinogenicity model accepted for the testing of topical pharmaceuticals employs the albino hairless Crl:SKH1-hr BR mouse (P. D. Forbes et al., *Photobiology.* 663-669 (E. Riklis ed., 1991)).

After administration of a topical formulation, experimental protocols typically instruct that mice be irradiated once daily, five days per week, for 40 weeks. Intensity and cumulative UV radiation dose is measured in Robertson-Bergen Units (RBU). The RBU is a measure of biological effectiveness for UVR, with 400 RBU being approximately one minimal erythema dose in previously untanned human skin, i.e., about 30 $mJ/cm^2$ in a sun-sensitive skin type I or II. Mouse carcinogenicity studies are completed at 600 RBU per week because this produces an appropriate tumor mean latent period for comparison with test article treated and untreated controls. At this radiation level, about half of the untreated animals will have a first perceptible tumor by week forty-one. A higher control UVR level of 1200 RBU per week results in a significant reduction in the median tumor latent period. At this radiation dose, about half of the untreated animals will have a first perceptible tumor by week twenty-four. Animals continue to be observed for 12 weeks after 40 weeks of product application to provide a total of 52 weeks of tumor data.

At least two common topical therapies promote tumor formation in this UV induced mouse carcinogenicity model. Benzoyl peroxide and retinoids such as tretinoin, which are commonly used to treat acne, promote the formation of skin tumors compared to untreated or vehicle controls. (*Physicians Desk Reference,* 56th Edition, Medical Economics Company, Inc., Montvale N.J., (2002)). While many topical products containing these actives are currently in use, the patients who use them are strongly encouraged to avoid sun exposure on their face after using the product. However, significantly shielding the face from sun exposure, especially for young adults, is virtually impossible for products that are often used twice daily.

U.S. Pat. Nos. 6,113,888 to Castro et al.; U.S. Pat. No. 6,200,964 to Singleton et al.; and U.S. Pat. No. 6,231,837 to Stroud et al. describe topical compositions that contain therapeutics. However, the therapeutic is not included to provide protection from ultraviolet radiation. If UVR protection is desired, sunscreens are added to the formulations.

Topical compositions including dapsone have been described in U.S. Pat. Nos. 5,863,560 and 6,060,085 to Osborne, and U.S. application Ser. No. 10/081,050 to Osborne, which are herein incorporated by reference in their entirety. However, these compositions were formulated to treat acne, not to prevent skin damage from UV radiation.

Therefore, new compositions that protect against UV-induced skin damage are needed.

SUMMARY OF THE INVENTION

The present invention is a method for protecting against UV radiation-induced skin damage in individuals by selecting individuals in need of protection from UV radiation and administering to them a composition that includes dapsone. In general, selection of the individual in need of protection from UV radiation is based upon factors such as the frequency and duration of UV radiation exposure, e.g., sun exposure, and/or the risk of the individual for UV-induced skin damage. In turn, the risk is typically assessed by examining such factors as the individual's age and predisposition to sunburn or develop pigmented lesions after sun exposure, any genetic predisposition to skin cancer, prior medical history of UV-induced skin damage, and presentation of UV-induced skin damage at the time of examination.

The dapsone compositions may be provided in formulations including, but not limited to, gels, creams, lotions, solutions, hydrophilic or hydrophobic ointments, microemulsions, shake-powders, aerosol and pump sprays, tablets, capsules, patches, films, and suppositories. The dapsone used in the compositions may be in dissolved or particulate form, or a mixture of dissolved and microparticulate dapsone. The composition that is administered may also include additives such as preservatives, antioxidants, fragrances, or colorants.

Besides protecting against signs of aging (e.g., wrinkles) and hyperpigmentation, compositions including dapsone may be administered to protect against the formation, in other words, prevent the development of, UV-induced premalignant skin lesions such as actinic keratosis, as well as UV-induced malignant tumors of the skin. In another embodiment, the dapsone compositions may be administered to individuals having at least one premalignant skin lesion to prevent the premalignant skin lesion from becoming a malignant skin tumor.

DETAILED DESCRIPTION OF THE INVENTION

Figure 1:
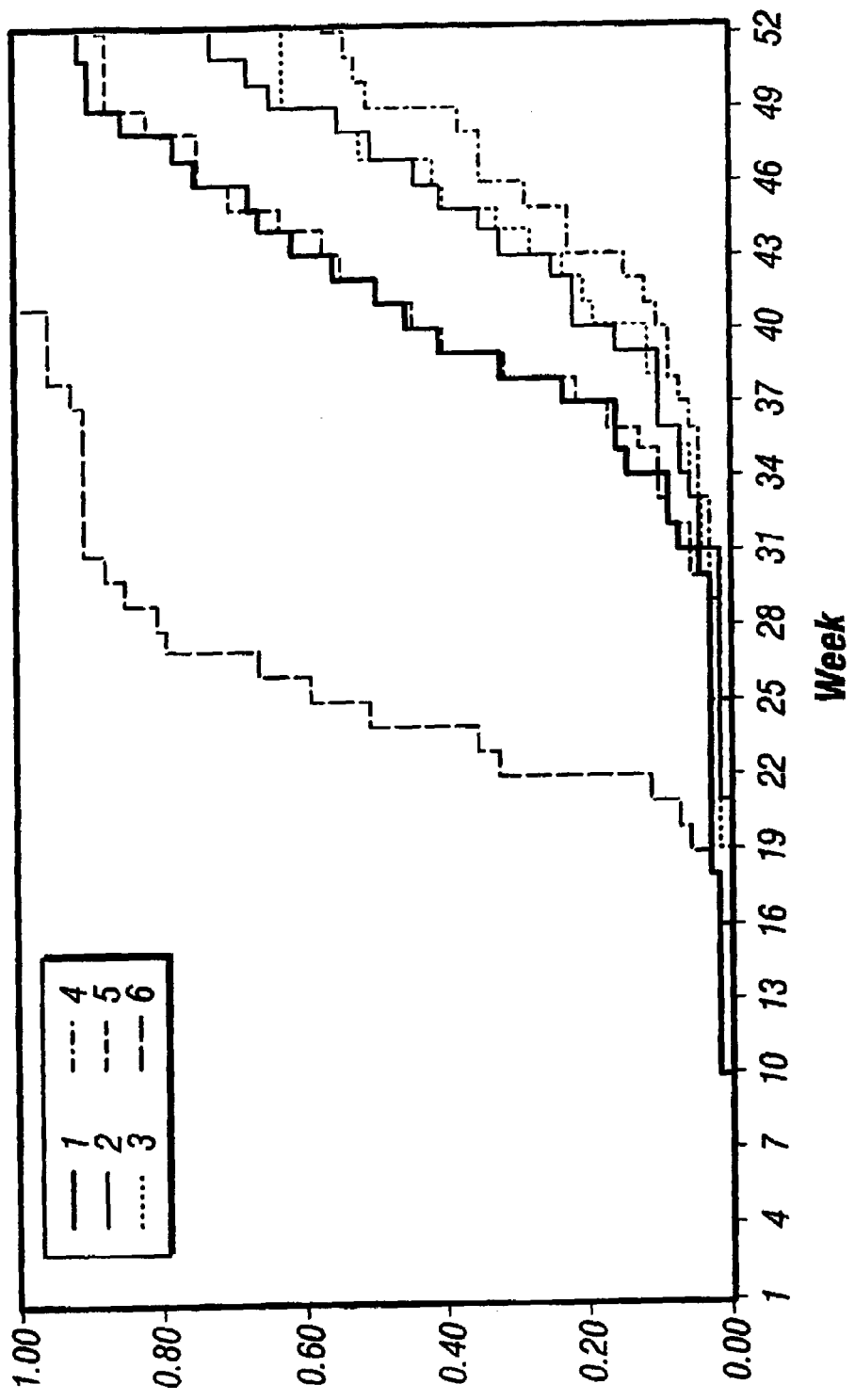
FIG. 1 shows a decrease in prevalence of tumor formation in albino hairless mice exposed to UVR at 600 and 1200 RBU with the use of various topical dapsone compositions.

The inventive methods provide dapsone compositions that protect against ultraviolet radiation-induced skin damage.

As used herein, the terms "UV-induced skin damage" or "UV-induced skin disorder" do not refer to acne. These terms are used interchangeably and refer to skin damage resulting from exposure to ultraviolet light in the A (320-400 nm), B (290-320 nm), or C ranges (200-290 nm). Examples of UV-induced skin damage, also referred to herein as "skin lesions", include wrinkles, hyperpigmentation, dysplasias such as actinic keratosis, and malignant skin tumors such as squamous cell or basal cell carcinoma.

As used herein, the term "protects" or "protecting" refers to a reduction in the amount of skin damage which can be manifested, e.g., by a decrease in the number and/or severity of individual skin lesions, or prevention of the development of skin lesions.

The term "topical" as used herein refers to the route of administration of a composition that involves direct application to the body part being treated, e.g., the skin for dermatological compositions. Examples of topical application include application to the skin of gels or other semisolids to rub-on, solutions to spray, or liquids to be applied by an applicator. Rinse-off application with washes, cleansers, or shampoos are also examples of topical application. Typically, areas of the body suitable for application of compositions having dapsone include the skin of the face, throat, neck, scalp, chest, back, ears, and other skin sites where sun exposure may occur.

By use of the term "dapsone" it is meant the chemical compound dapsone having the chemical formula $C_{12}H_{12}N_2O_2S$ as well as bis(4-aminophenyl)sulfone, 4',4'-diaminodiphenyl sulfone and its hydrates, 4,4'-sulfonylbis-benzeneamine, 4,4'-sulfonyldianiline, diaphenylsulfone, dapsone analogs, and dapsone related compounds. "Dapsone analogs" refers to chemical compounds that have similar chemical structures and thus similar therapeutic potential to dapsone such as the substituted bis(4- aminophenyl)-sulfones. "Dapsone related compounds" refers to chemical compounds that have similar therapeutic activity, but are not as closely related by chemical structure to dapsone such as the substituted 2,4-diamino-5-benzylpyrimidines.

Dapsone Compositions

Dapsone Topical Gel

The topical gel compositions of this invention utilize various forms of dapsone. For instance, in one embodiment, dapsone may be present in the composition as only dissolved dapsone. In another embodiment, dapsone may be present in the composition only as microparticulate dapsone. In a further embodiment, the dermatological composition exhibits an optimal balance between dissolved dapsone that is available to cross through the stratum corneum to become systemically available, and microparticulate dapsone that is retained in or above the stratum corneum to serve as a reservoir or to provide dapsone to the supracorneum zone. The microparticulate dapsone may comprise a crystalline precipitant or an amorphous precipitant.

In one embodiment, the dermatological composition that is applied comprises a semi-solid or gel-like vehicle that may include a polymer thickener, water, preservatives, active surfactants or emulsifiers, antioxidants, sunscreens, and a solvent or mixed solvent system. The solvent or mixed solvent system is important to the formation of the microparticulate to dissolved dapsone ratio. The formation of the microparticulate, however, should not interfere with the ability of the polymer thickener or preservative systems to perform their functions.

Polymer thickeners that may be used include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Preferably, the gelling agent comprises between about 0.2% to about 4% by weight of the composition. More particularly, the preferred compositional weight percent range for "CARBOPOL®" is between about 0.5% to about 2%, while the preferred weight percent range for "NATROSOL®" and "KLUCEL®" is between about 0.5% to about 4%. The preferred compositional weight percent range for both "HYPAN®" and "STABILEZE®" is between about 0.5% to about 4%.

"CARBOPOL®" is one of numerous cross-linked acrylic acid polymers that are given the general adopted name carbomer. These polymers dissolve in water and form a clear or slightly hazy gel upon neutralization with a base such as sodium hydroxide, potassium hydroxide, triethanolamine, or other amine bases. "KLUCEL®" is a cellulose polymer that is dispersed in water and forms a uniform gel upon complete hydration. Other preferred gelling polymers include hydroxyethylcellulose, hydroxypropylcellulose, cellulose gum, MVA/MA copolymers, MVE/MA decadiene crosspolymer, PVM/MA copolymer, or a combination thereof.

Preservatives may also be used in this dermatological composition and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

In one embodiment, the dermatological composition that is applied includes 0.5% to 4.0% carbomer and about 0.5% to 10% dapsone that exists in both a dissolved state and a microparticulate state. In another embodiment, the dermatological composition comprises about 1% carbomer, about 80-90% water, about 10% (diethylene glycol monoethyl ether (DGME), about 0.2% methylparaben, and about 0.3% to 3.0% dapsone including both microparticulate dapsone and dissolved dapsone, and about 2% of a base. More particularly, the carbomer may include "CARBOPOL® 980" and the base may include sodium hydroxide solution.

In a another embodiment, the composition comprises dapsone and ethoxydiglycol, which allows for an optimized ratio of microparticulate drug to dissolved drug. This ratio determines the amount of drug delivered, compared to the amount of drug retained in or above the stratum corneum to function in the supracorneum domain. The system of dapsone and DGME may include purified water combined with "CARBOPOL®" gelling polymer, methylparaben, propylparaben, titanium dioxide, BHA, and a base to neutralize the "CARBOPOL®."

Dapsone Topical Cream or Lotion

In another embodiment, dapsone may be applied as a topical cream or lotion in which dapsone may be dissolved or dispersed or both partially dissolved and partially dispersed. Topical creams or lotions may be either oil-in-water emulsions or water-in-oil emulsions. The oil phase may include but is not limited to fatty alcohols, acids, or esters such as cetyl palmitate, cetyl alcohol, stearyl alcohol, stearic acid, isopropyl stearate, glycerol stearate, mineral oil, white petrolatum, or other oils alone or in combination. The topical creams or lotions may be formulated for use as sunscreens.

Emulsifiers that may be added to the composition include, but are not limited to, steareth 20, ceteth 20, sorbitan sesquioleate, sorbitan mono-oleate, propylene glycol stearate, dosium lauroyl sarcosinate, polysorbate 60, or combination. Preservatives, antioxidants, fragrances, colorants, thickeners, and other additives required to achieve a pharmaceutically or cosmetically acceptable or preferred product may also be included. However, topical creams and lotions are not limited to these components since one skilled in the art will be aware of additional components useful in the formulation of topical creams and lotions.

Dapsone Topical Solution or Suspension

In another embodiment, dapsone may be applied as a solution or suspension. These are fluid solvent or mixed-solvent systems including, but not limited to, water, ethanol, propylene glycol, glycerol, polyethylene glycol, ethyl acetate, propylene carbonate, n-methylpyrrolidone, triethanolamine, 1,4-butanediol, triacetin, diacetin, dimethyl isosorbide alone or in combination. Preservatives, antioxidants, fragrances, colorants, thickeners, suspending agents, enhancers, and other additives required to achieve pharmaceutically or cosmetically acceptable or preferred product may also be included. Again, topical solutions or suspensions are not limited to these components, since one skilled in the art will be aware of additional components useful in the formulation of topical solutions or suspensions.

Additional Dapsone Formulations

Dapsone may also be topically applied using a pharmaceutical or cosmetic carrier form such as a hydrophobic or hydrophilic ointment, roll-on or stick product, microemulsion, shake powder, an aerosolized spray or mousse, a pump spray or mousse, or bath additive. Examples of ointments include essentially non-aqueous mixtures of petrolatum, lanolin, polyethylene glycol, plant or animal oils, either hydrogenated or otherwise chemically modified. An ointment may also contain a solvent in which dapsone is either fully or partially dissolved. Additional pharmaceutical carriers will be known to those skilled in the art and this list should not be considered to be limiting.

In addition to topical compositions, dapsone may be formulated as pharmaceutical preparations including, but not limited to, granules, tablets, suppositories, capsules, suspensions, patches, films, and aerosols. Pharmaceutical grade organic or inorganic carriers and/or diluents suitable for inhalation or oral, parenteral, transmucosal, or transdermal administration may be used to formulate compositions including dapsone. Stabilizing agents, wetting and emulsifying agents, salts for varying the osmotic pressure, or buffers for securing an adequate pH value may also be included in the dapsone compositions.

Administration of Dapsone Compositions

In addition to topical administration, dapsone, dapsone analogs, or dapsone related compounds may have sufficient partitioning to the skin or sufficient activity in the skin to be delivered by other routes of administration. For example, systemic dosing may accompany topical dosing, or systemic dosing for the purpose of photoprotection may be used as a singular therapy. Other routes and methods of administration will be known to those skilled in the art. These include, but are not limited to, oral, rectal, vaginal, nasal, ocular, oral transmucosal and other transmucosal, transdermal, parenteral, and pulmonary routes. Parenteral administration includes, without limitation, intravenous, subcutaneous, intramuscular, intra-arterial, intrathecal, and intraperitoneal administration. Pulmonary delivery may be achieved by nebulization, aerosol inhalation, or dry powder inhalation. Products developed for administration using these alternate delivery routes will have compositions recognized by those skilled in the art, as described in *Remington: The Science and Practice of Pharmacy*, 19th Edition, Mack Publishing Company, Easton Pa., (1995).

In one variation, the dapsone compositions are administered to protect individuals against UV-induced skin damage such as sunburn, malignant skin tumors, premalignant lesions, and wrinkles. Typically, the dapsone compositions are administered once daily, but may be administered more frequently if desired. In another variation, the dapsone compositions are administered to prevent premalignant skin lesions from progressing to malignant skin tumors in individuals.

The dapsone compositions are administered to selected individuals. By "selected" it is meant individuals in whom UV protection is considered desirable because of age, frequent or long duration of exposure to UV radiation, e.g., sun, and/or because they possess an increased risk for UV radiation-induced skin damage. For example, individuals at increased risk are those who are more prone to sunburn or develop pigmented lesions after sun exposure, or who due to genetic makeup, have a condition that predisposes them to skin cancer, e.g., xeroderma pigmentosum. Furthermore, individuals with a prior medical history of a UV-induced skin disorder or who present with UV-induced skin damage at the time the need for UV protection is determined are at increased risk.

The dapsone compositions are typically administered before the individual engages in an activity that involves UV radiation exposure. The activity may be an outdoor activity such as sunbathing, walking, running, swimming, biking, and the like, engaged in for purposes of recreation or physical fitness. The dapsone compositions may also be administered to individuals engaging in indoor activities, e.g., indoor tanning or laboratory work that involves exposure to ultraviolet light.

Method for Preparing the Dapsone Dermatological Composition

In general, the method for producing a dermatological gel composition having dissolved dapsone and microparticulate dapsone precipitates comprises the steps of completely dissolving dapsone in a solvent or solvent mixture; adding and adequately dispersing a polymeric thickener in water; and combining the dissolved dapsone with the dispersed polymeric thickener. Alternatively, water may be slowly added to the dissolved dapsone, followed by the addition of a polymeric thickener. Ethoxydigylcol and 1-methyl-2-pyrollidone are preferred solvents for use in the topically applied dermatological composition.

In one embodiment, the method for preparing a topically applied dermatological composition having dissolved and microparticulate dapsone comprises the steps of forming a homogenous dispersion by stirring purified water vigorously enough to form a vortex and sifting gel polymer into the vortex formed in the water while continuing to stir; forming a pharmaceutical component by dissolving methyl paraben and propylparaben in DGME by mixing to form a solution, and mixing dapsone with the solution until the pharmaceutical is dissolved; mixing the pharmaceutical component with the homogenous dispersion to form a microparticulate dapsone dispersion; and adding a caustic material.

In another embodiment, the method for preparing a topically applied dermatological composition having only dissolved dapsone includes the steps of dissolving dapsone in an oil phase or mixed solvent system. The dissolved dapsone is then combined with the water phase of an emulsion or thickeners or other cosmetic or pharmaceutical excipients to form a dermatological product. This topical cream, lotion, solution, ointment or other topical formulation will contain only dissolved dapsone at ambient conditions.

In yet another embodiment, the method for preparing a topically applied dermatological composition having primarily dispersed dapsone includes the step of dispersing dapsone in a water phase, non-solvating solvent or mixed solvent system. The dispersed dapsone is then combined with the oil phase of an emulsion or thickeners or other cosmetic or pharmaceutical excipients to form a dermatological product. This topical cream, lotion, suspension, ointment or other topical formulation will contain dispersed dapsone particles and minimal (less than about 5%) dissolved dapsone at ambient conditions.

The order in which reagents are combined may be important, depending on the particular reagents necessary for the target mixture. For example, after a pharmaceutical such as dapsone is dissolved in a solvent such as DGME, water may be slowly added to the dapsone in the DGME solution, or the dapsone in DGME solution may be added to the water with mixing. Adding the dapsone in DGME solution to water may result in less polydispersity in the size of the microparticulates than adding water to the dapsone in DGME solutions. The carbomer is generally dispersed in the water component of the formulation, while the remaining ingredients will be dissolved or dispersed in whichever of the two components are best for dissolving or dispersing the ingredient. For example, it is suggested to dissolve methylparaben, propylparaben, and BHA in DGME. After the DGME component and water component are combined, neutralizer is added to formulate the gel.

EXAMPLES

The following example is provided to show that dapsone has an unexpected protective benefit in the treatment of ultraviolet radiation-induced skin tumors.

Those skilled in the art will recognize that while specific embodiments have been illustrated and described, various modifications and changes may be made without it departing from the spirit and scope of the invention.

Example 1

Effect of Dapsone on Skin Tumor Formation in Mice

Example 1 demonstrates the protective effect of dapsone on UV-induced skin tumor formation. Male and female albino hairless Crl:SKH1-hrBR mice (36/sex/group) were obtained from Charles River Laboratories (Wilmington, Mass.) and individually housed in custom-designed stainless steel irradiation cages.

The experimental dapsone formulations (50 µl/mouse, Monday through Friday) were administered to the dorsum and sides of the mice to an area of approximately 25 cm$^2$ using a glass rod, and the mice irradiated once daily, 5 days per week, for 40 weeks. Aqueous carbomer gels containing 1% dapsone/10% DGME (diethylene glycol monoethyl ether); 3% dapsone/17.5% DGME; or 5% dapsone/25% DGME were chosen from range-finding studies. A vehicle control aqueous carbomer gel contained 25% DGME. Formulations were administered one hour before irradiation on Monday, Wednesday, and Friday and one hour after irradiation on Tuesday and Thursday. Mice were then maintained without being dosed for an additional 12 weeks for a total of 52 weeks.

The simulated solar radiation (SSR) source was a 6.5 kilowatt zenon long arc water-cooled burner, filtered by a 1 mm thick Schott WG 320 doped glass filter. During exposure the mice were continuously monitored by a customized detector, which records both intensity and cumulative UVR dose in Robertson-Berger Units (RBU, 400 RBU approximates one minimal erythema dose (MED) in previously untanned human skin). The low UVR calibration group (120 RBU/daily, 600 RBU/week) produced an appropriate tumor median latent period for comparison with other groups. The high UVR calibration group (240 RBU/day, 1200 RBU/ week) produced a significant decrease in median tumor latent period. The test level of UVR (600 RBU per week) permits detection of a modified photocarcinogenic response by the test system in response to a test article. Over the course of the study, the daily UVR dose was consistent and the total dose across groups was appropriate.

All mice were observed for viability at least twice daily, and weekly for general skin observations. Other clinical observations were recorded weekly; body weights were recorded weekly for the first 13 weeks, and then every four weeks thereafter and at sacrifice. Individual UV-induced skin tumor data (size and location) were electronically recorded. Any mouse bearing a tumor>10 mm planar diameter was sacrificed. Furthermore, all mice in a group were sacrificed when:

1) fewer than 50% of the mice per sex survived;
2) more than 50% of the surviving mice in the group had tumors of at least 4 mm (planar diameter); and
3) the Study Director reviewed the data and approved the sacrifice.

Tables, graphs, and statistical testing of tumor data were provided as output from the ROELEE program (P. N. Lee Statistics and Computing, Ltd., Sutton, United Kingdom). Group comparisons of tumor prevalence were based on the methods described by Peto and colleagues (Peto, R., et. al. (1980). Guidelines for Simple, Sensitive Significance Tests for Carcinogenic Effects in Long-Term Animal Experiments. *IARC Monographs, Supplement* 2. *Long-Term and Short-Term Screening Assays for Carcinogens: A Critical Appraisal*).

Since bi-directional effects on carcinogenicity are plausible, testing was based on two-tailed probabilities (i.e., the null hypothesis states that the superimposed variable does not alter carcinogenicity). Evaluations were based on two-group comparisons. Statistical interpretation was based primarily on tumors at least 1 mm in diameter using the following descriptive parameters:

1. "Median Onset" or "Median Week to Tumor": The time at which one-half of the members of other groups have acquired one or more qualifying tumors, and the associated 95% confidence interval. Separate estimates evaluated "biased" medians (based on survivors) and mortality-adjusted medians.
2. "Mortality-Free Prevalence": The proportion of mice in a group exhibiting one or more qualifying tumors, as a function of time, and adjusted for the effects of competing mortality. This descriptor is the complementary probability to the Kaplan-Meier "probability of survival without a tumor" and is derived form calculations of the Kaplan-Meier type (Kaplan, E. L., and Meier, P. *J. Am. Stat. Assoc.* 53:457-481 (1958)).
3. "Tumor Yield": The number of tumors present, divided by the number of surviving mice (i.e., average number of tumors per mouse).
4. "Survival": The absolute number of mice alive at the time of observation, compared to the initial number in each group.

Table 1 shows that the Unbiased Median Weeks to Tumor was unaffected by the vehicle formulation (25% DGME vehicle), and delayed in groups administered the dapsone formulations and exposed to 600 RBU/week. The group exposed to high UVR (1200 RBU/week), served as a positive control to show that the Unbiased Median Weeks to Tumor was accelerated. The unbiased median latent period was not achieved by the end of the study for the 3% dapsone/17.5% DGME gel group, or for the 5% dapsone/25% DGME gel group for male mice. An entry of 53 weeks is used in Table 1 to illustrate this fact. Dapsone increased the Unbiased Median Weeks to Tumor in a dose-dependent manner, indicating a reduction in the photocarcinogenic response of the mice to UVR in these groups.

FIG. 1 shows the prevalence by week of the first 1 mm tumor for the sexes combined. In comparison with the 25% DGME vehicle formulation administration (line 1), all dapsone containing gels (line 2, 1% dapsone gel; line 3, 3% dapsone gel; line 4, 5% dapsone gel) significantly reduced the development of skin tumors in mice exposed to 600 RBU/week for the sexes combined ($p<0.001$ for 1%, 3%, and 5% dapsone gel), in male mice (data not shown, $p<0.01$ for 1% dapsone gel, and $p<0.001$ for 3% dapsone gel, and $<0.001$ for 5% dapsone gel), and in female mice (data not shown, $p<0.01$ for 1% and 3% dapsone gel and $p<0.001$ for 5% dapsone gel). The prevalence of 1 mm tumor formation in untreated mice exposed to 600 RBU/week (line 5) paralleled that of mice administered the 25% DGME vehicle formulation (line 1). Line 6 demonstrates the increase in skin tumor formation in untreated mice exposed to 1200 RBU/week.

The Tumor Potency Ratio (TPR) expresses the influence of a test article on the skin's response to UVR exposure. The concept of TPR depends on the relationship between the weekly UVR dose, as a measure of stimulus rate, and the chosen response measure of Unbiased Median Week to Tumor for each group (tumors>1 mm). With those values and the dose rate calibration for the untreated 600 RBU/week and 1200 RBU/week groups, the apparent radiation dose rate of the groups was calculated. The difference from the nominal rate represents the effect of a test variable on UVR dose delivery. Since unbiased median latent period was not achieved by the end of the study (52 weeks) for the 3% dapsone gel group, or the 5% dapsone gel group for males, the estimated TPR was calculated from the estimated unbiased median latent period of 53 weeks. As shown in Table 2, the TPR was reduced with dapsone application in a dose-dependent manner in sexes combined, indicating a dose-dependent inhibitory effect on UVR-induced skin tumor production. The vehicle formulation had no effect on TPR.

Furthermore, biologically important and/or statistically significant reductions occurred in erythema, edema, flaking and/or thickening in the groups of male and/or female mice administered dapsone formulations (data not shown).

In sum, the administration of the vehicle or dapsone formulations did not enhance photocarcinogenesis; rather, the dapsone formulations protected against UV radiation-induced skin tumor development. This conclusion is supported by the tumor endpoints Unbiased Median Weeks to Tumor, Peto Analysis of Tumor Onset, Prevalence Curves, Tumor Yield per Survivor and Tumor Potency Ratio. These observations also suggest a reduction in the UV radiation-induced inflammatory process in the groups administered the dapsone formulations.

All publications and patent applications cited in this application are herein incorporated by reference in their entirety. Although the foregoing invention has been described by way of illustration and example for purposes of clarity and understanding, it will be readily apparent to those of ordinary skill in the art in light of the teachings of this invention that certain changes and modifications may be made thereto without departing from the spirit or scope of the appended claims.

TABLE 1

Unbiased Median Weeks to Tumor for Tumors ≧ 1 mm

| Formulation | 25% DGME Vehicle | 1% Dapsone in a 10% DGME Gel | 3% Dapsone in a 17.5% DGME Gel | 5% Dapsone in a 25% DGME Gel | None | None |
|---|---|---|---|---|---|---|
| UVR Exposure RBU/Week | 600 | 600 | 600 | 600 | 600 | 1200 |
| Sexes Combined (weeks) | 41.5 | 47.50 | 48.00 | 49.00 | 41.50 | 24.50 |
| Males (weeks) | 45.25 | 50.00 | 53.00 | 53.00 | 44.00 | 25.00 |
| Females Median (weeks) | 39.50 | 45.00 | 45.50 | 49.00 | 39.50 | 24.00 |

TABLE 2

Tumor Potency Ratios (≧1 mm Tumor Size)

| Formulation | 25% DGME Vehicle | 1% Dapsone in a 10% DGME Gel | 3% Dapsone in a 17.5% DGME Gel | 5% Dapsone in a 25% DGME Gel | None | None |
|---|---|---|---|---|---|---|
| UVR Exposure RBU/Week | 600 | 600 | 600 | 600 | 600 | 1200 |
| Sexes Combined | 1.00 | 0.84 | 0.83 | 0.80 | 1 | 2 |
| Males | 1.06 | 0.97 | 0.85 | 0.80 | 1 | 2 |
| Females Median | 1.00 | 0.86 | 0.82 | 0.74 | 1 | 2 |

The invention claimed is:

1. A method for protecting against ultraviolet radiation-induced skin damage in an individual comprising:
   a) selecting an individual in need of protection from ultraviolet radiation; and
   b) administering a composition topically, transmucosally or transdermally to the individual, wherein said composition comprises dapsone so as to protect against ultraviolet radiation-induced skin damage.

2. The method of claim 1 wherein said individual is in need of protection from a malignant skin in tumor.

3. The method of claim 2 wherein said individual is in need of protection from squamous cell carcinoma.

4. The method of claim 2 wherein said individual is in need of protection from basal cell carcinoma.

5. The method of claim 1 wherein said individual is in need of protection from a premalignant skin lesion.

6. The method of claim 5 wherein said individual is in need of protection from actinic keratosis.

7. The method of claim 1 wherein said composition is administered before said individual engages in an activity, wherein said activity exposes said individual to ultraviolet radiation.

8. The method of claim 7 wherein said activity is an outdoor activity.

9. The method of claim 8 wherein said activity is sunbathing.

10. The method of claim 8 wherein said activity is swimming.

11. The method of claim 8 wherein said activity is running.

12. The method of claim 7 wherein said activity is an indoor activity.

13. The method of claim 12 wherein said activity is tanning.

14. The method of claim 1 wherein said composition is a semi-solid aqueous gel.

15. The method of claim 1 wherein said composition is a cream.

16. The method of claim 1 wherein said composition is a lotion.

17. The method of claim 1 wherein said composition is a solution.

18. The method of claim 1 wherein said composition is an ointment.

19. The method of claim 1 wherein said composition is a spray.

20. The method of claim 1 wherein said composition further comprises an additive selected from the group consisting of a preservative, an antioxidant, a fragrance, and a colorant.

21. The method of claim 1 wherein said composition comprises at least about 1% dapsone.

22. The method of claim 1 wherein said composition comprises at least about 3% dapsone.

23. The method of claim 1 wherein said composition comprises at least about 5% dapsone.

24. A method for protecting against a premalignant skin lesion from becoming a malignant skin tumor comprising administering a composition topically, transmucosally or transdermally to an individual having at least one premalignant skin lesion, wherein said composition comprises dapsone so as to protect against a premalignant skin lesion from becoming a malignant skin tumor.

25. A method for protecting against UV-induced malignant skin tumor formation in an individual comprising:
   a) selecting the individual in need of protection from UV radiation; and
   b) administering a composition topically, transmucosally or transdermally to the individual, wherein said composition comprises dapsone so as to protect against UV-induced malignant skin tumor formation.

* * * * *

UNITED STATES PATENT AND TRADEMARK OFFICE
CERTIFICATE OF CORRECTION

PATENT NO. : 7,399,462 B2  Page 1 of 1
APPLICATION NO. : 11/011291
DATED : July 15, 2008
INVENTOR(S) : Osborne It is certified that error appears in the above-identified patent and that said Letters Patent is hereby corrected as shown below:

On the Title Page, Item (56), under "Foreign Patent Documents", line 4, after "6/2001" delete "WO  WO-02/053138 A2  07/2002".

On the Title Page, Item (56), under "Other Publications", line 1, delete "S.Stockel," and insert -- S.Stöckel, et al., --, therefor.

On the Title Page, Item (56), under "Other Publications", lines 6-8, after "328-331." delete "Stöckel, S., et al., "Dapsone-Induced Photodermatitis in a Patient With Linear IgA Dermatosis", European Journal of Dermatology, 11, (Jan.-Feb. 2001), 50-53.".

In column 5, line 30, delete "(diethylene" and insert -- diethylene --, therefor.

In column 5, line 36, after "In" delete "a".

In column 5, line 60, delete "dosium" and insert -- sodium --, therefor.

In column 7, line 38, delete "Ethoxydigylcol and 1-methyl-2-pyrollidone" and insert -- Ethoxydiglycol and 1-methyl-2-pyrrolidone --, therefor.

In column 8, line 58, delete "zenon" and insert -- xenon --, therefor.

In column 11, line 36, in Claim 2, after "skin" delete "in".

Signed and Sealed this

Sixteenth Day of September, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,399,462 B2 | Page 1 of 1 |
| APPLICATION NO. | : 11/011291 | |
| DATED | : July 15, 2008 | |
| INVENTOR(S) | : Osborne | |

It is certified that error appears in the above-identified patent and that said Letters Patent is hereby corrected as shown below:

On the Title Page Item (56), under "Foreign Patent Documents", line 4, after "6/2001" delete "WO    WO-02/053138 A2    07/2002".

On the Title Page Item (56), under "Other Publications", line 1, delete "S.Stockel," and insert -- S.Stöckel, et al., --, therefor.

On the Title Page Item (56), under "Other Publications", lines 6-8, after "328-331." delete "Stöckel, S., et al., "Dapsone-Induced Photodermatitis in a Patient With Linear IgA Dermatosis", European Journal of Dermatology, 11, (Jan.-Feb. 2001), 50-53.".

In column 5, line 30, delete "(diethylene" and insert -- diethylene --, therefor.

In column 5, line 36, after "In" delete "a".

In column 5, line 60, delete "dosium" and insert -- sodium --, therefor.

In column 7, line 38, delete "Ethoxydigylcol and 1-methyl-2-pyrollidone" and insert -- Ethoxydiglycol and 1-methyl-2-pyrrolidone --, therefor.

In column 8, line 58, delete "zenon" and insert -- xenon --, therefor.

In column 11, line 36, in Claim 2, after "skin" delete "in".

Signed and Sealed this

Twenty-third Day of September, 2008

JON W. DUDAS
*Director of the United States Patent and Trademark Office*